United States Patent [19]
Lecuyer et al.

[11] Patent Number: 5,843,013
[45] Date of Patent: Dec. 1, 1998

[54] VALVE FOR THE TREATMENT OF HYDROCEPHALUS

[75] Inventors: Alain Lecuyer, Grasse; Christian Sainte-Rose, Vanves, both of France

[73] Assignee: Cordis S.A., Viry Chatillon, France

[21] Appl. No.: 824,249

[22] Filed: Mar. 25, 1997

[30] Foreign Application Priority Data

Mar. 26, 1996 [FR] France .................................. 96 03726

[51] Int. Cl.⁶ ....................................................... A61M 5/00
[52] U.S. Cl. ................................................................ 604/9
[58] Field of Search ............................. 604/8, 9, 10, 247

[56] References Cited

U.S. PATENT DOCUMENTS 4,781,672 11/1988 Hooven .
5,520,632 5/1996 Leveen et al. .
5,643,195 7/1997 Drevet et al. ................................ 604/9

FOREIGN PATENT DOCUMENTS 2698535 6/1994 France .

*Primary Examiner*—David Isabella
*Attorney, Agent, or Firm*—Dennison, Meserole, Pollack & Scheiner

[57] ABSTRACT

A valve for the treatment of hydrocephalus of the type including a membrane provided with an aperture and demarcating within a housing an upstream chamber and a downstream chamber. A rod of variable cross section attached to a stopper penetrates into the aperture. According to the invention, the housing includes three parts, a first body, a second body and a base cap. The first body and second body are assembled so as to squeeze the periphery of the membrane. The first body, the stopper and a first face of the membrane form one of the chambers, and the second body, the base cap and the other face of the membrane form the other chamber.

4 Claims, 6 Drawing Sheets

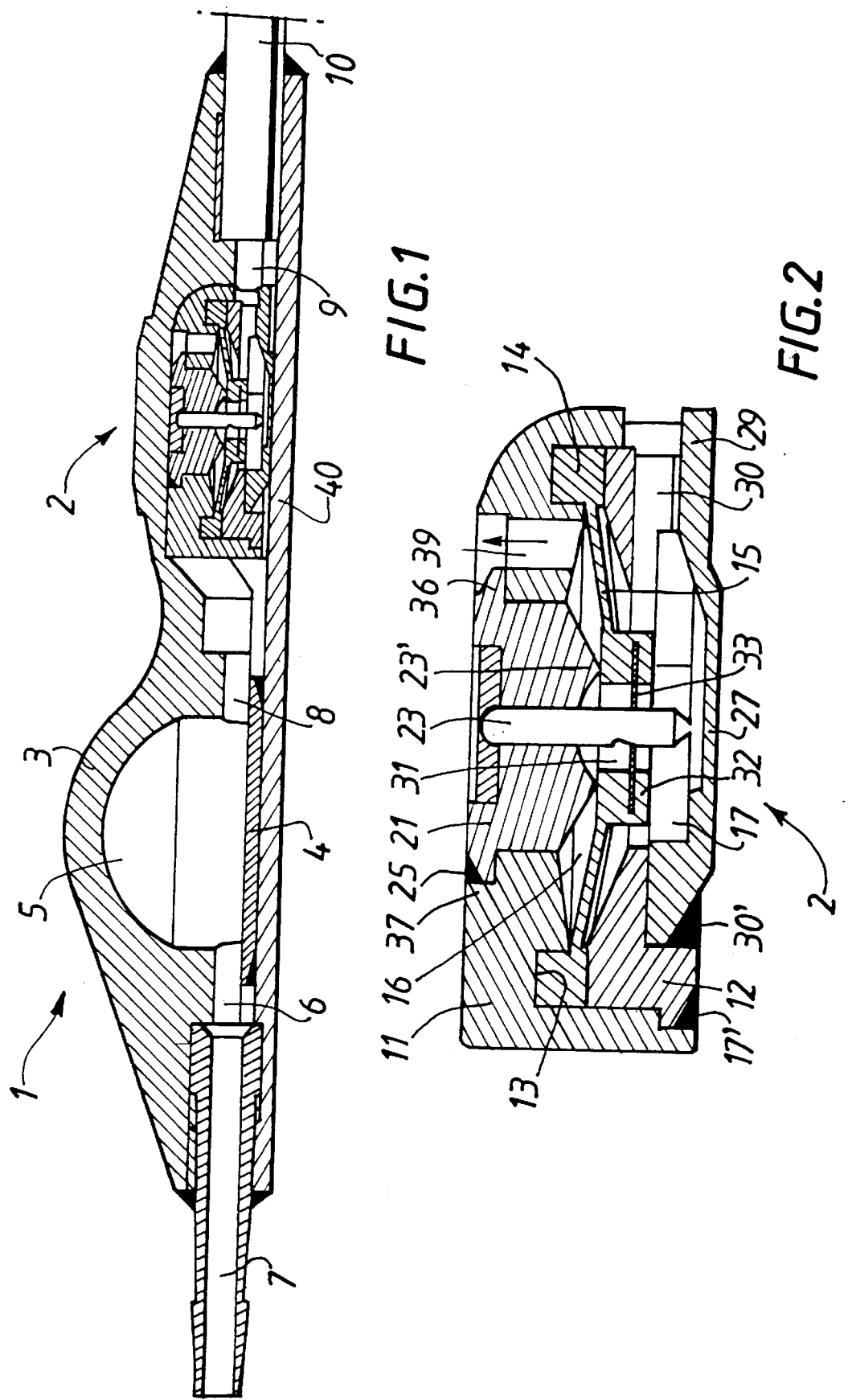

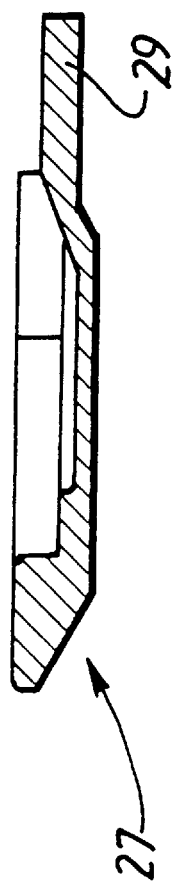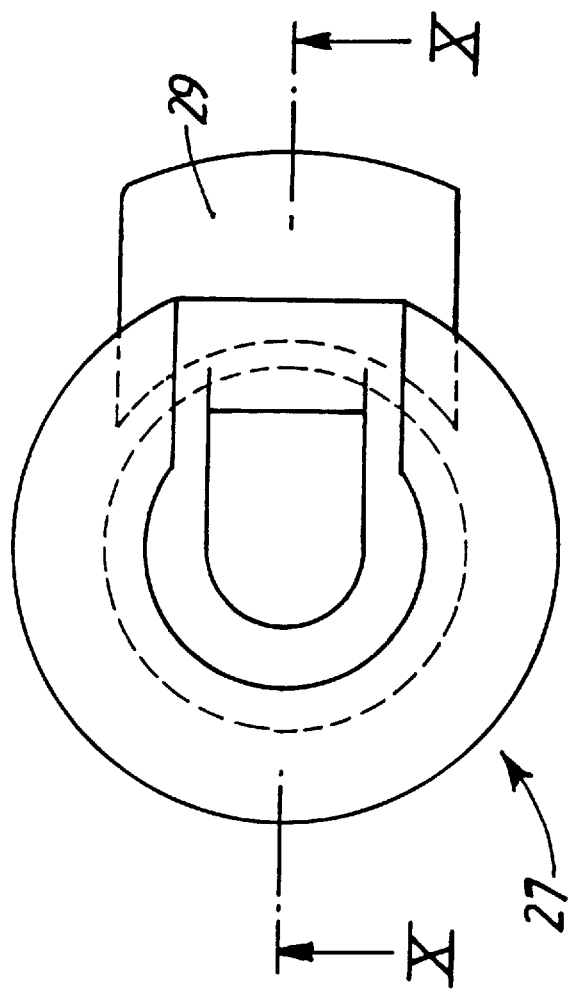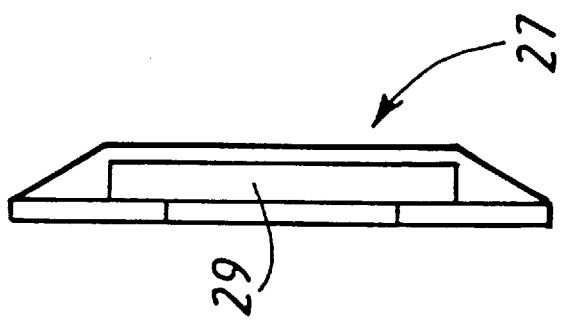

VALVE FOR THE TREATMENT OF HYDROCEPHALUS

BACKGROUND OF THE INVENTION

The present invention concerns a valve for the treatment of hydrocephalus, and more particularly such a valve of the kind comprising:

a housing forming a cavity;

a separating membrane mounted at its periphery on the housing, provided with an aperture and demarcating within the said cavity an upstream chamber and a downstream chamber, the said membrane having a first and a second face;

the said housing forming, in the upstream chamber, a seat for the membrane, the said seat surrounding the said aperture;

a rod with a variable cross-section arranged so as to penetrate into the said aperture;

the said housing having an aperture receiving a stopper, the rod being mounted in firm attachment to this stopper.

Such valves are already known, notably from the document U.S. Pat. No. 4781672.

Valves of this kind are known to feature multi-zone operation. Initially, no flowing takes place so long as the differential pressure between the upstream chamber and the downstream chamber is insufficient to detach the membrane from its seat.

Then the rod profile is such that a zone begins to form in which the differential pressure remains almost constant as the flow-rate increases rapidly. Once a given so-called valve control flow-rate is reached, the pressure increases while the flow-rate remains substantially constant.

Finally, beyond a certain differential pressure threshold, the unattached end of the rod withdraws from the membrane aperture. The result is a maximum differential pressure, which is practically independent of the flow-rate which increases in response to demand.

In known valves of this kind, the housing is made up of two half-housings which squeeze the periphery of the membrane when they are assembled, prior to their adhesion. The top part of the top half-housing itself is open, with its opening threaded inwardly.

The stopper is threaded outwardly and fixedly receives the rod. The stopper is then installed in the aperture of the top half-housing, and screwed more or less deeply so that the rod runs into the membrane aperture in an appropriate manner and the required pressure/flow-rate characteristic is obtained.

Although they are satisfactory, these valves present drawbacks arising from the fact that their production, and above all adjustment, is complex and a simplification thereof would be desirable.

SUMMARY OF THE INVENTION

The present invention is designed to overcome these drawbacks.

To this end, the object of the invention is a valve for the treatment of hydrocephalus, of the kind described above, characterized in that:

the housing is made up of three parts, a first and a second body which squeeze the periphery of the membrane when they are assembled, and a base cap which, together with the second body and the second membrane face, demarcates one of the chambers;

and that the aperture is formed in the first body, the stopper being fixedly adapted to it to demarcate the other chamber with the said first body and the first membrane face.

Thus the various parts of the housing, the base cap and the stopper are easy to slide into each other, and if necessary adhere, with adjustments being possible during assembly, rather than after assembly by screwing the stopper in or out, as was the case in prior art.

More particularly, the stopper and the rod firmly attached to it may be installed before the base cap, and adjustments may be carried out by any suitable means through the area of the base left open. The base is then mounted after adjustments are made.

In one particular embodiment, the chamber demarcated by the stopper, the first body and the first membrane face is the upstream chamber, the downstream chamber being demarcated by the base cap, the second body and the second membrane face.

Advantageously, the body demarcating the downstream chamber has a conical bearing surface for the membrane in the position it occupies when the valve is fully open.

Thus in the event of greatly excess pressure, the membrane bears on this conical surface, and so avoids any risk of damage.

In a preferred embodiment, the body demarcating the upstream chamber has on its outside a substantially circular channel through which the liquid to be drained is admitted, the said channel communicating via a plurality of holes with the said upstream chamber.

This circular channel enables homogeneity to be achieved in the entry flow into the valve, as the liquid penetrates into the upstream chamber by the set of holes set out along the membrane periphery.

BRIEF DESCRIPTION OF THE DRAWINGS

A description will now be offered, on a non-limiting exemplary basis, of a particular embodiment of the invention, with reference to the appended schematic drawings, wherein:

FIG. 1 is a sectional view of a drainage assembly for the treatment of hydrocephalus, comprising a valve according to the invention;

FIG. 2 is a sectional view in the same planes, on a larger scale, of the valve shown in FIG. 1;

FIG. 3a is placed over FIG. 3b, an exploded perspective view of the valve shown in FIG. 2;

FIG. 10 is a sectional view along line X—X of FIG. 11 of the base cap of the valve in FIG. 2;

FIG. 11 is a top view of the base cap in FIG. 10, and

FIG. 12 is a right-hand view of the base cap in FIGS. 10 and 11.

DESCRIPTION OF THE PREFERRED EMBODIMENTS

Figure 3A:
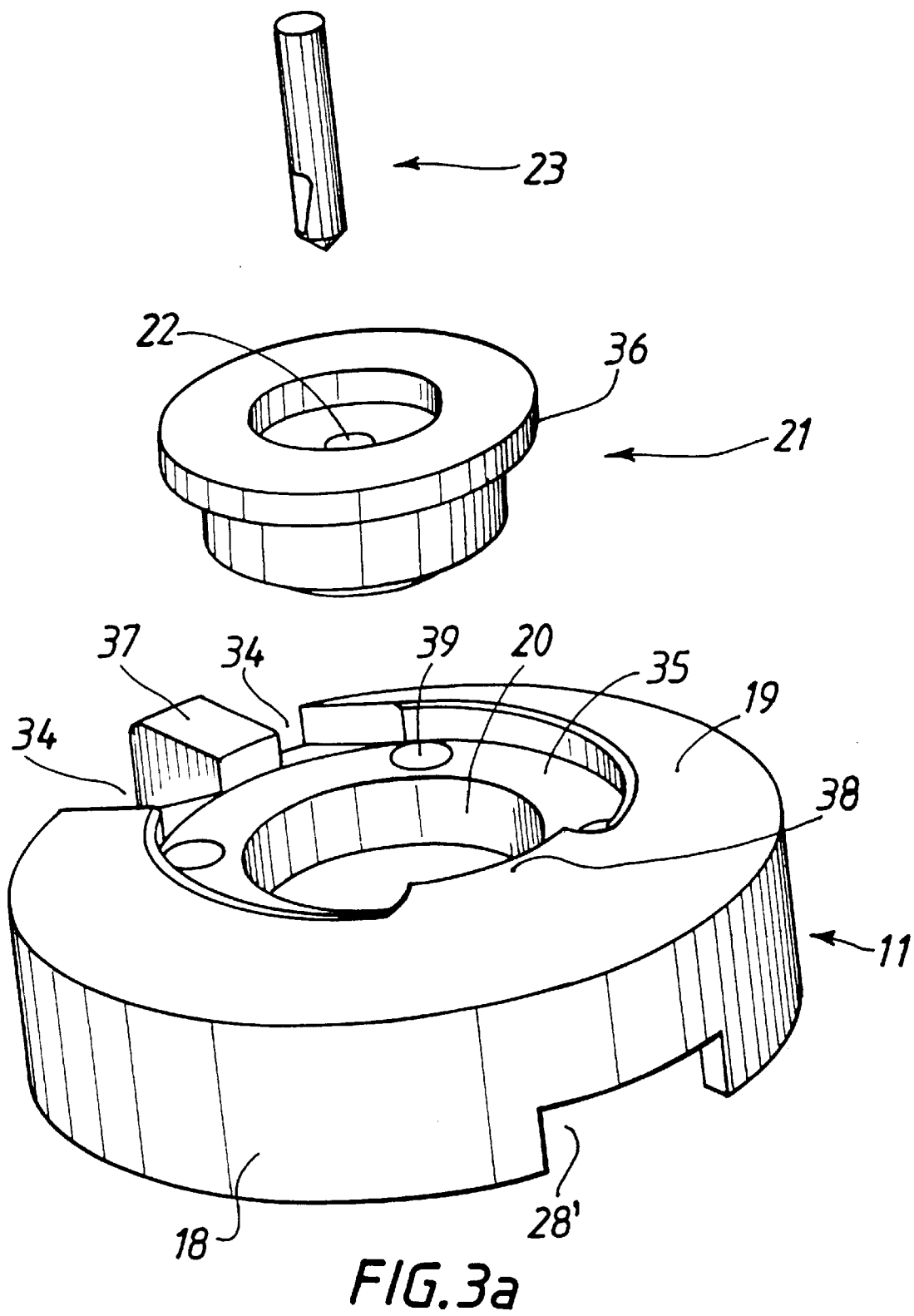
FIGS. 3a and 3b represent, when

FIG. 1 shows an assembly made up of an injection site 1 and a valve 2 according to the invention.

The injection site basically comprises a dome 3 of synthetic material which is flexible and which may be pierced with a hypodermic needle, demarcating with a base 4 a chamber 5 connected by an upstream channel 6 to a catheter fitting 7, and by a downstream channel 8 to the inlet to the valve 2. A catheter which is not shown has one of its ends mounted on the fitting 7 and its other end is unattached and so may be guided to the ventricle which is to be drained. The outlet of the valve 2 is connected by a channel 9 to a drainage catheter 10, the unattached end of which may be guided into the drainage zone.

The injection site 5 permits, when the downstream channel 8 is flattened, an injection to be made into the ventricle and when the upstream channel 6 is flattened, the valve 2 to be cleaned.

Figure 3B:
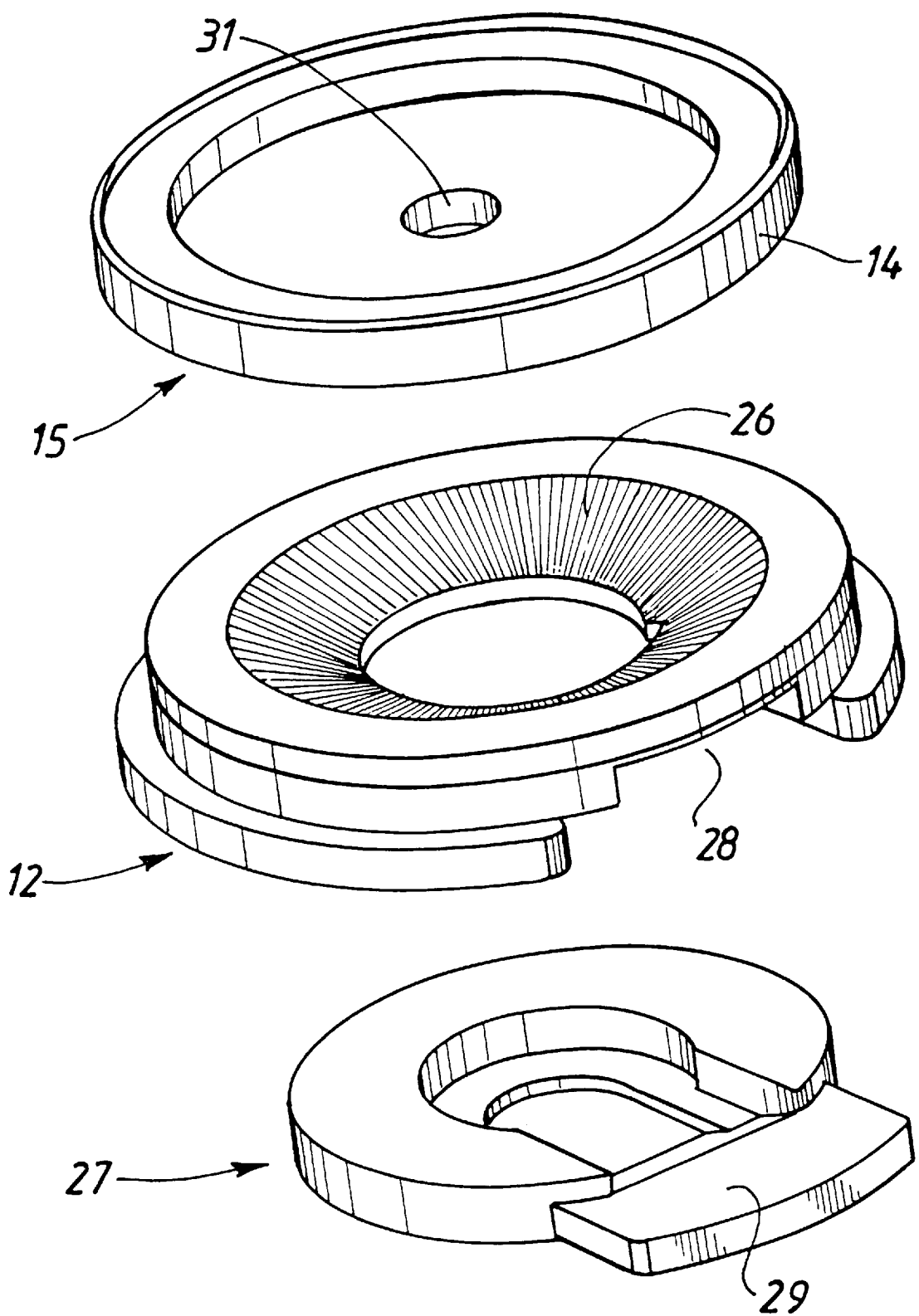
Figure 5:
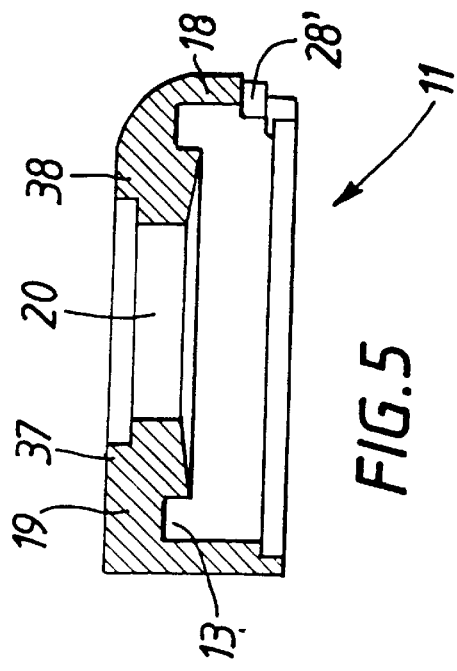
FIG. 5 is a sectional view along line V—V of FIG. 6.
Figure 4:
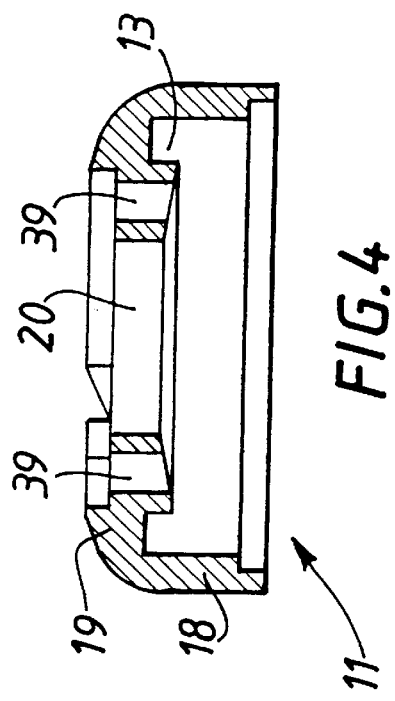
FIG. 4 is a sectional view along line IV—IV of FIG. 6, of the top housing body of the valve in FIG. 2.
Figure 6:
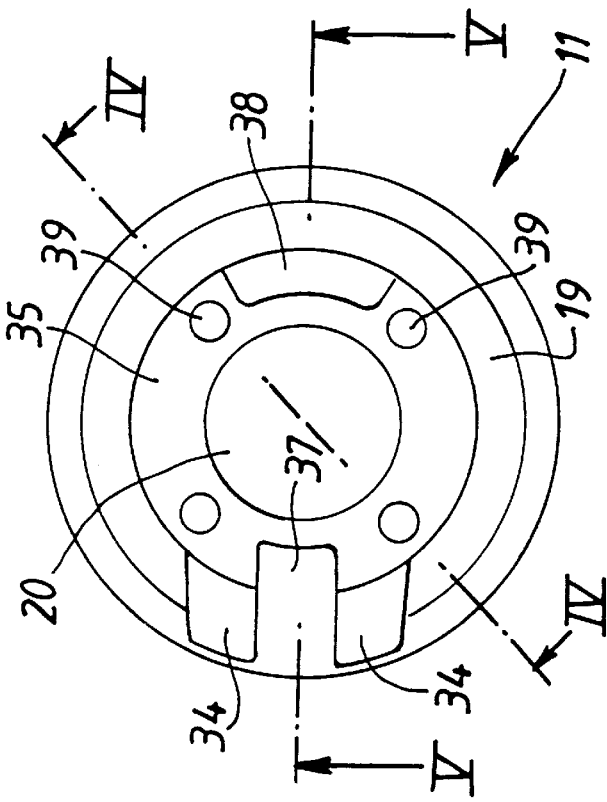
FIG. 6 is a top view of the housing body in FIGS. 4 and 5.
Figure 8:
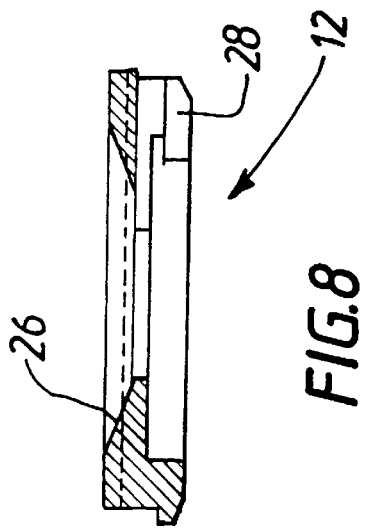
FIG. 8 is a sectional view along line VIII—VIII of FIG. 7.
Figure 7:
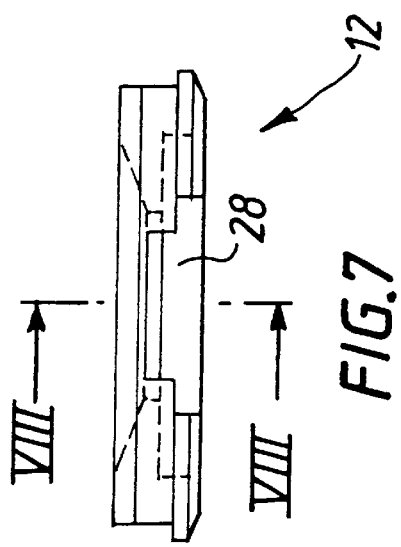
FIG. 7 is a front view of the lower housing body of the valve in FIG. 2.
Figure 9:
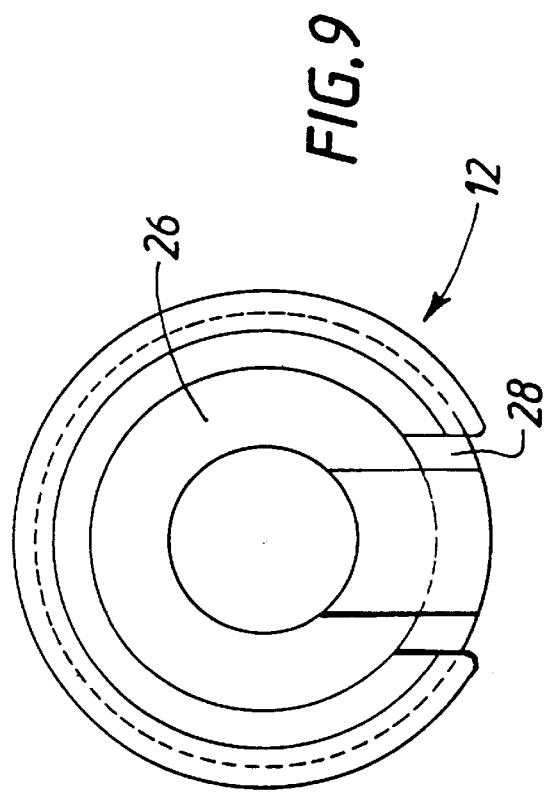
FIG. 9 is a top view of the housing body of FIGS. 7 and 8.

Referring now to FIGS. 2 and 3, it may be seen that the valve 2 comprises a top body 11 and a bottom body 12. The top body 11 forms an annular groove 13 to receive an edge flange 14 of a disk-shaped flexible membrane 15. The top body 11 and the membrane 15 demarcate an upstream chamber 16 and the bottom body 12 and the membrane 15 demarcate a downstream chamber 17. Thus the upstream and downstream chambers are separated by the membrane 15. The two bodies are held together by adhesion points 17'.

The top body 11 has a general crucible shape with a substantially cylindrical lateral wall 18 and a base 19 in which a circular aperture 20 is formed. The aperture 20 is closed by a stopper 21 bearing, in a central bore 22, a machined rod 23. In addition, the stopper 21 forms, around the rod 23, a seat 23' for the membrane 15 which presses thereon so long as the differential pressure between the chambers 16 and 17 remains inferior to a predetermined threshold. A resin 24 holds the rod 23 in the bore 22 and adhesion points 25 hold the stopper 21 in the aperture 20.

The bottom body 12 has a generally annular shape with a top bearing surface 26, facing the membrane 15, substantially a truncated cone and ribbed. A base cap 27 fits into the bottom body 12 to close the downstream chamber 17. A section 28 cut out of the bottom body 12 demarcates, with a section 28' cut out of the top body 11 and an extension 29 of the cap 27, an outlet channel 30 for the valve 2. Adhesion points 30' hold the base cap 27 on the bottom body 12.

The membrane 15 has a central aperture 31 edged by a flange 32. When the stopper 21 is in place, the machined end of the rod 23 passes through the aperture. An annular washer 33 is engaged in a circular groove formed in the cylindrical inner wall of the flange 32.

The liquid enters the valve via two lateral channels 34 formed in the wall of the top body 11. These channels 34 open into an annular channel 35 blocked, at two diametrically opposite points, by a shoulder 36 of the stopper 21 and by two projections 37 and 38 from the top body 11. Thus the channel 35 forms two branches. Each of these branches communicates with the upstream chamber via two holes 39 formed in the base 19 of the top body 11.

The various components described above are assembled in an appropriate order, but the base cap 27 is mounted last. Thus while this cap is not yet in place, the valve may be adjusted, and more particularly the washer 33 may be centred relative to the axis of the rod 23.

Once the valve 2 has been fully assembled, it is installed in a receiving unit provided for this purpose and made in one piece of plastics material, which also forms the dome 3 of the injection site. Then a base plate 40, the fitting 7 and the catheter are each installed to complete the assembly.

The valve described above operates in the same way as the valves of a known kind and in the way described above.

What is claimed:

1. A valve for the treatment of hydrocephalus comprising:

a housing including a first body and a second body, said first and second body defining an aperture therein;

a separating membrane defining an outer periphery and said membrane having a membrane aperture formed therein, the separating membrane being mounted at said outer periphery within said housing between said first body and second body such that the membrane defines an upstream chamber and a downstream chamber, said upstream chamber having a seat surrounding said aperture for receiving said separating membrane;

a stopper configured for receipt in said aperture;

a base cap configure to engage one of said upstream and downstream chamber;

wherein said stopper, said first body and a first face of said separating membrane defines one of said downstream and upstream chamber, and said base cap, said second body and a second face of said separating membrane defining the other of said chambers;

a rod having a variable cross section mounted to the stopper and positioned to penetrate into said membrane aperture, the rod controlling liquid flow between said upstream and said downstream chambers.

2. A valve as claimed in claim 1, wherein the chamber defined by the stopper, the first body and the first membrane face is the upstream chamber, the downstream chamber being defined by the base cap, the second body and the second membrane face.

3. A valve as claimed in claim 1, wherein the body demarcating the downstream chamber has a conical bearing surface for the membrane in the position occupied thereby when the valve is fully open.

4. A valve as claimed in claim 1, wherein the body defining the upstream chamber has on its outside a substantially circular channel through which liquid to be drained is admitted, said channel communicating via a plurality of holes with said upstream chamber.

* * * * *